United States Patent [19]

Chambon

[11] Patent Number: 5,202,395
[45] Date of Patent: Apr. 13, 1993

[54] MANUFACTURING PROCESS CONTROL AND PRODUCT CHARACTERIZATION

[75] Inventor: François Chambon, Brussels, Belgium

[73] Assignee: Exxon Chemical Patents Inc., Linden, N.J.

[21] Appl. No.: 716,193

[22] Filed: Jun. 17, 1991

[30] Foreign Application Priority Data

Mar. 11, 1991 [GB] United Kingdom ............... 9105078

[51] Int. Cl.⁵ ............................................. C08F 2/00
[52] U.S. Cl. ................................... 526/60; 526/348; 73/54.09; 73/54.14
[58] Field of Search ............... 526/60; 73/54, 55, 56

[56] References Cited

U.S. PATENT DOCUMENTS

4,241,602 12/1980 Han et al. ............................. 73/56

*Primary Examiner*—Joseph L. Schofer
*Assistant Examiner*—David Wu
*Attorney, Agent, or Firm*—William G. Muller; Myron B. Kurtzman; Catherine L. Bell

[57] ABSTRACT

The viscous and elastic components of a viscoelastic melt, for example a polymer melt, are examined to provide information useful in quality control in the process for the manufacture of the material. Measurement of the entrance pressure drop exhibited by the viscoelastic fluid when forced through a narrow die is shown to be an effective means of preparing polymers of differentiated property characteristics despite otherwise being similar in terms of commonly measured properties of molecular weight and melt index.

7 Claims, 6 Drawing Sheets

MANUFACTURING PROCESS CONTROL AND PRODUCT CHARACTERIZATION

This invention is based upon previously filed British Patent Application 9105078.1 filed Mar. 11, 1991.

BACKGROUND OF THE INVENTION

1. Field of the Invention

This invention relates to manufacturing processes, their control, and to measuring devices for use in the control of manufacture. More especially, it relates to monitoring polymerization processes, and to a control device embodying a rheometer or rheometers and the use of the device in controlling polymerization to obtain a polymer with desired properties.

2. Background Art

Although the invention will be described in detail with special reference to the manufacture of a synthetic polymer, it has utility in any application in which the rheological properties of a material in viscoelastic fluid form, for example in a melt, are related to the suitability of the material for a particular end use.

If a polymer, for example polyethylene, is to be suitable for certain applications, for example packaging film, it must satisfy certain requirements in processing and in final product quality. Film, for example, should be glossy and optically clear, i.e., free from haze, so that the contents of a package may be inspected and the package presents an attractive appearance to the customer. In addition to achieving these properties, it is also important to improve manufacturing rates without adversely affecting the quality of the product. Polymer melt properties may limit the rate of manufacture of commercially desirable products. The melt characteristics of the polymer affect the maximum production rates consistent with good quality product in, for example, melt-blowing film and extrusion coating processes.

It is known that the molecular weight distribution (MWD) and the degree of long chain branching (LCB) of a polyethylene are properties that affect the properties of the film made from such materials, and that there is a correlation between melt rheology and these properties—see Shida, et al., Polymer Engineering and Science, 17, 769, 1977. If clear film is desired, LCB is avoided, and/or MWD kept narrow, so far as possible. Conversely, when a high melt strength is required, as in extrusion coating, or the manufacture of thick or wide film, LCB and a wider MWD are desirable. In practice, polymer manufacturers have, however, employed melt index measurements or resorted to evaluating the optical properties of polymers such as polyethylene by blowing a film from a sample of the resin and measuring the haze.

The latter procedure has many disadvantages. Apart from its being an indirect measurement, with haze also possibly resulting from incorrect processing technique, as well as from the inherent properties of the polymer, measurement by film blowing and product inspection inevitably introduces a considerable time lag between the manufacture of polymer and its testing. The latter disadvantage also applies to melt index testing. Accordingly, considerable substandard quantities of polymer may have been produced, resulting in waste, before this fact is appreciated.

Patent literature contains certain disclosures of means for examining fluid material elasticity by use of pressure measurements conducted in narrow die systems. U.S. Pat. No. 4,241,602 addresses a continuous flow rheometer utilizing a slit or capillary tube for the measurement of pressure changes in a fluid with respect to viscosity and elasticity. The method taught utilizes pressure measurements within the capillary or slit for extrapolation of an exit pressure from which is calculated "first normal stress difference" which is said to be a measure of elasticity. U.S. Pat. No. 4,624,132 addresses rheometer design and a method of determining extensional viscosity and elasticity of molten polymer or other fluid by use of a combination of converging flow and diverging flow pressure measurements through capillary or slit dies having a particular configuration. The method is taught for use in design of machinery for the performance of polymer melt flow processing operations. Both designs presented contain complex configurations and require close attention to operational details thus permitting uncertainty of result and an unacceptable degree of reliability for use in manufacturing processes.

There accordingly remains a need for a more reliable and rapid method of measuring the rheological properties of a material to yield desired information about its structure.

There also remains a need for a simpler and more cost-effective method of obtaining information about a material's structure and integrating this information into the manufacturing process.

SUMMARY OF THE INVENTION

The invention provides a process for the manufacture of a polymer that is viscoelastic in the melt, or when otherwise in fluid form, which comprises supplying a feed comprising a monomer or monomers to a polymerization reactor, polymerizing the feed, recovering the resulting polymer from the reactor, monitoring the elasticity in fluid form of a sample of the polymer recovered from the reactor in terms of the entrance pressure drop through a narrow die, comparing said elasticity with a target elasticity or elasticity range set in the same terms and, if required, adjusting the polymerization process to produce polymer of target elasticity or elasticity range. Advantageously, the viscosity of the sample in fluid form is also monitored. Advantageously, the elasticity and if desired the viscosity of the polymer sample are measured on the polymer in the melt form, most advantageously by monitoring those properties during melt extrusion. Adjustment to reaction conditions, for example temperature, pressure, feed rate or composition, catalyst, the absence or presence, and if present their proportions, of chain branch suppressors or initiators, and polymerization promoters, is carried out to produce polymer of a target viscosity or viscosity range and elasticity or elasticity range.

DESCRIPTION OF PREFERRED EMBODIMENTS

Figure 1:
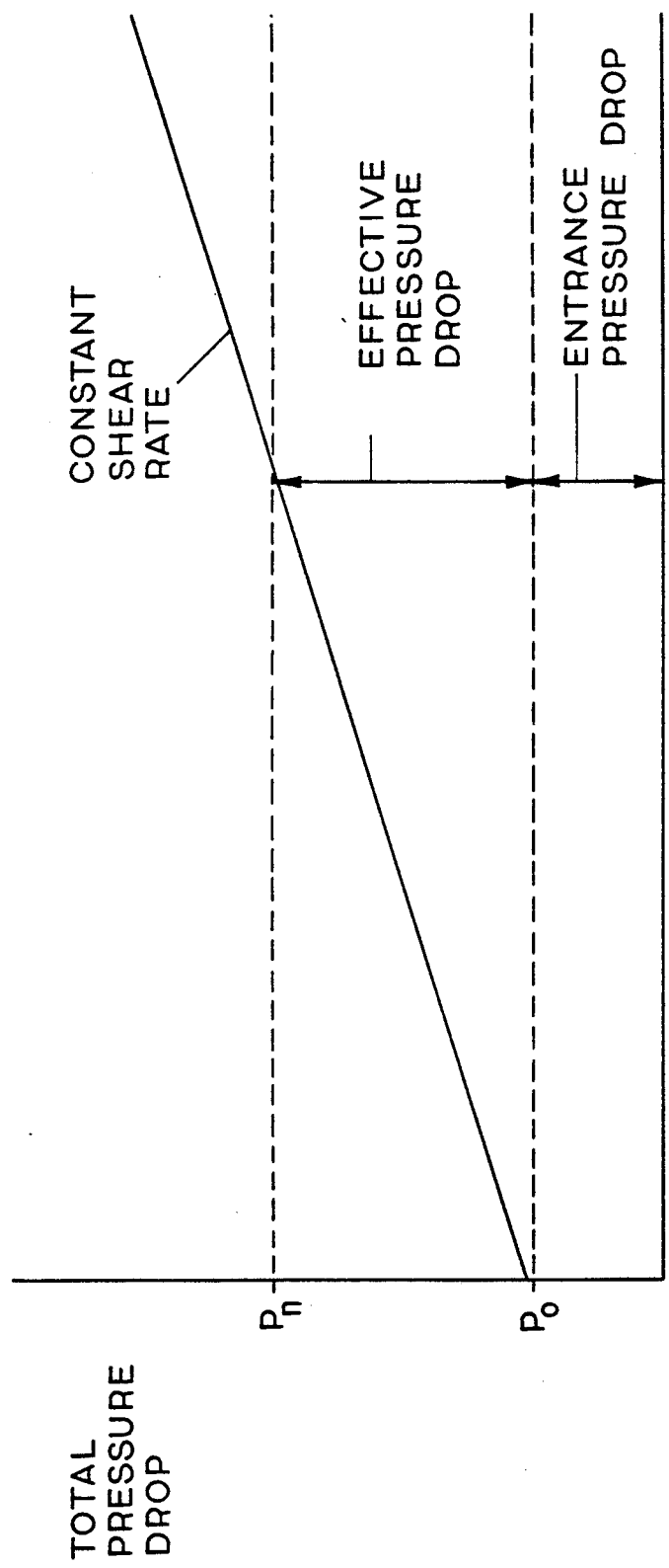
FIG. 1 is a schematic representation of the elastic and viscous components of the total pressure drop.

The invention provides a method of measuring and if desired or required controlling the elasticity of a viscoelastic material which comprises measuring the response of the material to shearing forces, the response of the material to extension forces, computing a function of the elasticity of the material from the measured responses, and if desired or required adjusting a variable in a process for manufacturing the material to provide material of a desired viscosity and elasticity.

The present invention further provides a device for measuring and if desired or required controlling the elasticity of a viscoelastic material which comprises means for measuring the response of the material to shearing forces, means for measuring the response of the material to extension forces, means for computing a function of the elasticity of the material from the measured responses, and if desired or required means for adjusting a variable in a process for manufacturing the material to provide material of a desired viscosity and elasticity.

The invention further provides apparatus for the manufacture of a polymer, comprising a polymerization reactor, means for controlling the reaction conditions within the reactor when in operation, means for recovering polymer from the reactor, melt-extrusion means, means for measuring rheological properties of polymer melt from the extrusion means, means for comparing the measured rheological properties with target rheological properties and means for varying the reaction conditions within the reactor in accordance with the results of the comparison.

According to the invention, there are provided a method for controlling a polymerization process in response to the values of melt viscosity and elasticity obtained by monitoring and an apparatus for use in the method.

One method of measuring the rheological properties of the material depends on the entrance effects that occur when the material flows from a reservoir into a narrow die, as used, for example, in commercial capillary tube or narrow slit viscometers. During passage through the capillary tube, for example, the material is subject largely to simple shear which, in the case of polymer molecules, causes tumbling and if any stretching of the molecule occurs it is local only.

At the entrance to the capillary, however, because the material is converging, the material is subjected to extension, which in the case of polymer molecules stretches or elongates them in the direction of movement.

The pressure drop between two points spaced along the length of a capillary tube or narrow slit is a measure of the energy dissipated as a result of friction between the molecules. The pressure drop on entry from the reservoir to the capillary or slit is a measure of the energy needed to stretch the molecules and is a useful correlation to the polymer melt elasticity. The pressure drop $P_{tot}$ along the total length of a narrow die may accordingly be divided into two components, $$P_{tot} = P_{ent} + P_{eff}$$

where $P_{ent}$ is the pressure drop at the convergent entrance to the die, and is dominated by the extension discussed above, and $P_{eff}$ is the pressure drop within the length of the die itself, dominated by the shear, these two elements representing the elastic and viscous components of the resistance to movement of the material under consideration.

The invention provides means for measuring these elements separately, which comprises means for measuring the pressure drop along the length of an elongate die and means for measuring the pressure drop at the entrance of a die. In a first embodiment, the entrance pressure drop is measured at the entrance of the elongate die. In a second, presently preferred, embodiment, the entrance pressure drop is measured at a second die the length of which is very small in comparison with its diameter, and is referred to hereinafter as a zero length die. The elongate die may be, for example, a capillary tube die or an elongate slit die, and in the second embodiment the zero length die may be in parallel or in series with the elongate die and in the latter case the two dies may be located in either order.

Although in principle if the shear rate through the die is constant, or if there are two dies the shear rates are the same, measurement at a single shear rate is sufficient, it is preferred to provide means for varying the throughput, and hence the shear rate, of the material.

For the elongate die, commercially available rheometers are available, for example a Göttfert Real Time Rheometer or a Rheometrics Melt Flow Monitor, which are normally supplied with a specified capillary die and slit die ratio respectively. Die ratios within the range of from 10:1 to 40:1 may conveniently be used. These rheometers are conventionally used for on-line measurement of melt index and in some cases melt viscosity.

For the "zero length" die, there may be used a die as described in more detail below, having a L/D ratio of 0.3:1. Other means suitable for measuring melt elasticity may also be used in accordance with the invention.

The invention is applicable to the manufacture of any material that under appropriate conditions forms a viscoelastic fluid. These conditions may arise in the course of manufacture or otherwise, and the invention is applicable to materials that are subsequently to undergo structural changes, for example crosslinking in polymers, that would interfere with or even prevent the formation of the viscoelastic state. The process may be applied more especially to the manufacture of thermoplastic polymers, including thermoplastic elastomeric polymers. As examples of polymers there may be mentioned olefin polymers, polyesters and polyamides and any of the known thermoplastic engineering polymers.

Among olefin polymers there may be mentioned olefin homopolymers, and copolymers of two or more olefins, or of one or more olefins and one or more other olefinically unsaturated monomers. As examples there may be mentioned polyethylene, polypropylene, ethylene/propylene copolymers, copolymers of ethylene with ethylenically unsaturated alcohols, acids, and esters, in which either the alcohol component or the acid (or anhydride) component may be unsaturated, e.g., ethylene/vinyl acetate, ethylene/ethyl acrylate, and ethyl/acrylic acid/ethyl acrylate copolymers.

Referring now to the drawings, and more especially to FIG. 1, there is shown the variation in pressure drop with the L/D ratio of a capillary die for a polymer melt at constant shear rate. As indicated above, the total pressure in an elongate die is made up of two elements, the effective pressure drop, $P_{eff}$, which is largely a function of melt viscosity, and the entrance pressure drop, $P_{ent}$, largely a function of melt elasticity, $P_{eff}$ falling to zero for a zero length die. The value of $P_{ent}$ for a given polymer depends, as indicated above, on polymer structure, which may be affected by polymerization reaction conditions.

Figure 2:
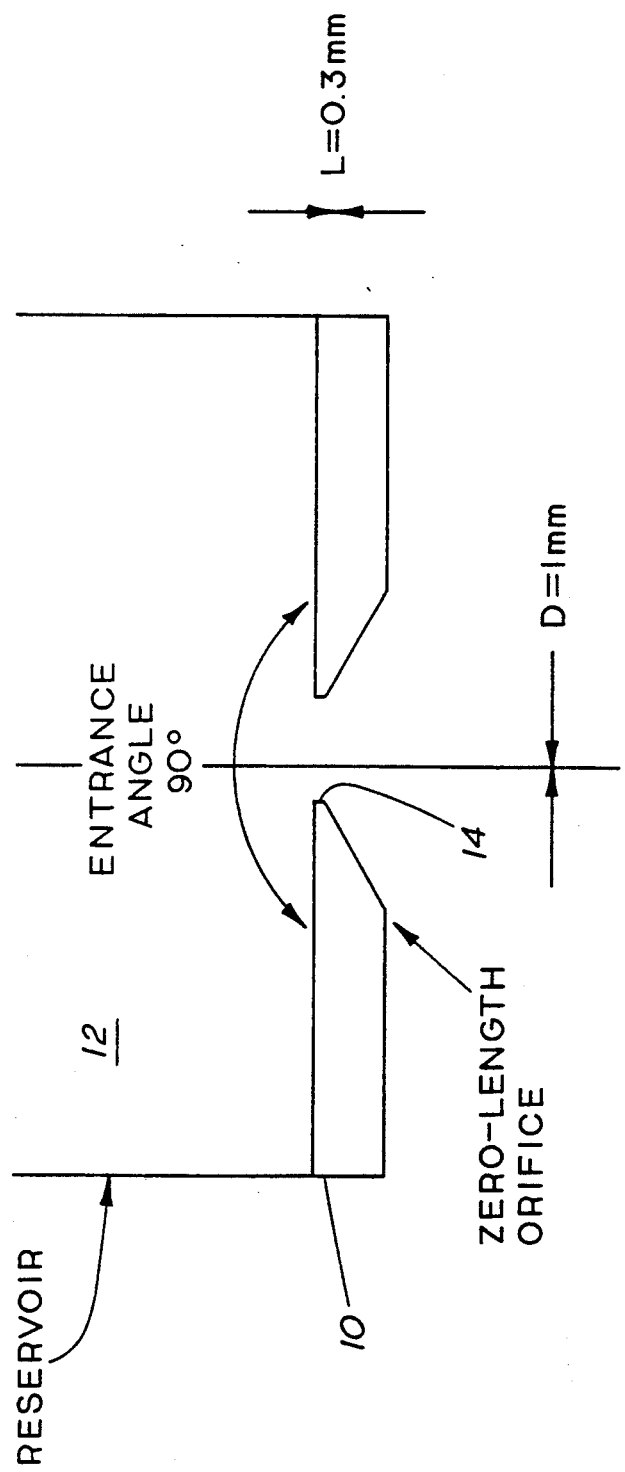
FIG. 2 shows in cross-section a "zero-length" die orifice.
Figure 3:
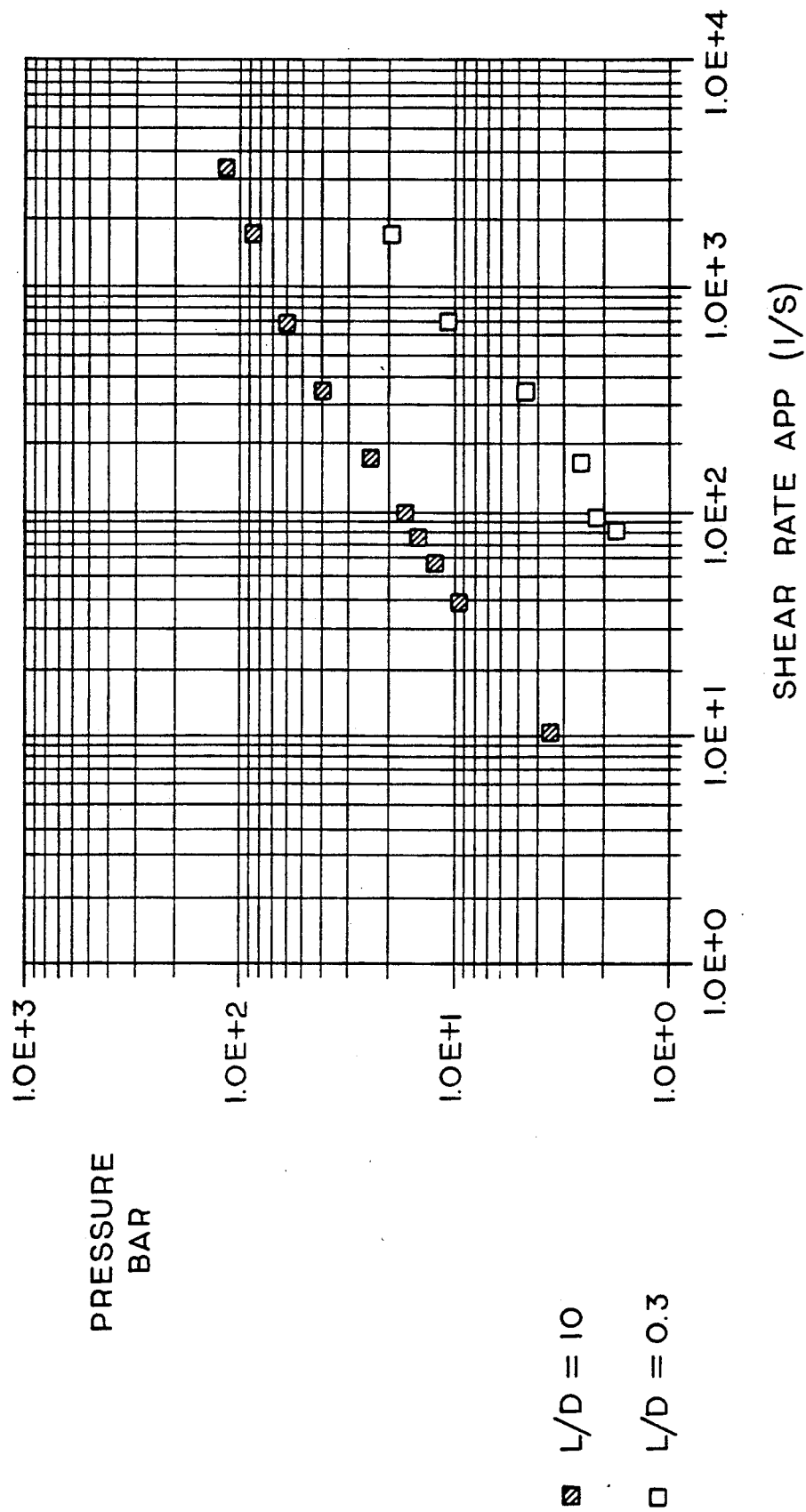
FIG. 3 shows the variation in measured pressure drop with apparent shear rate at dies with different L/D ratios for a low density polyethylene.
Figure 4:
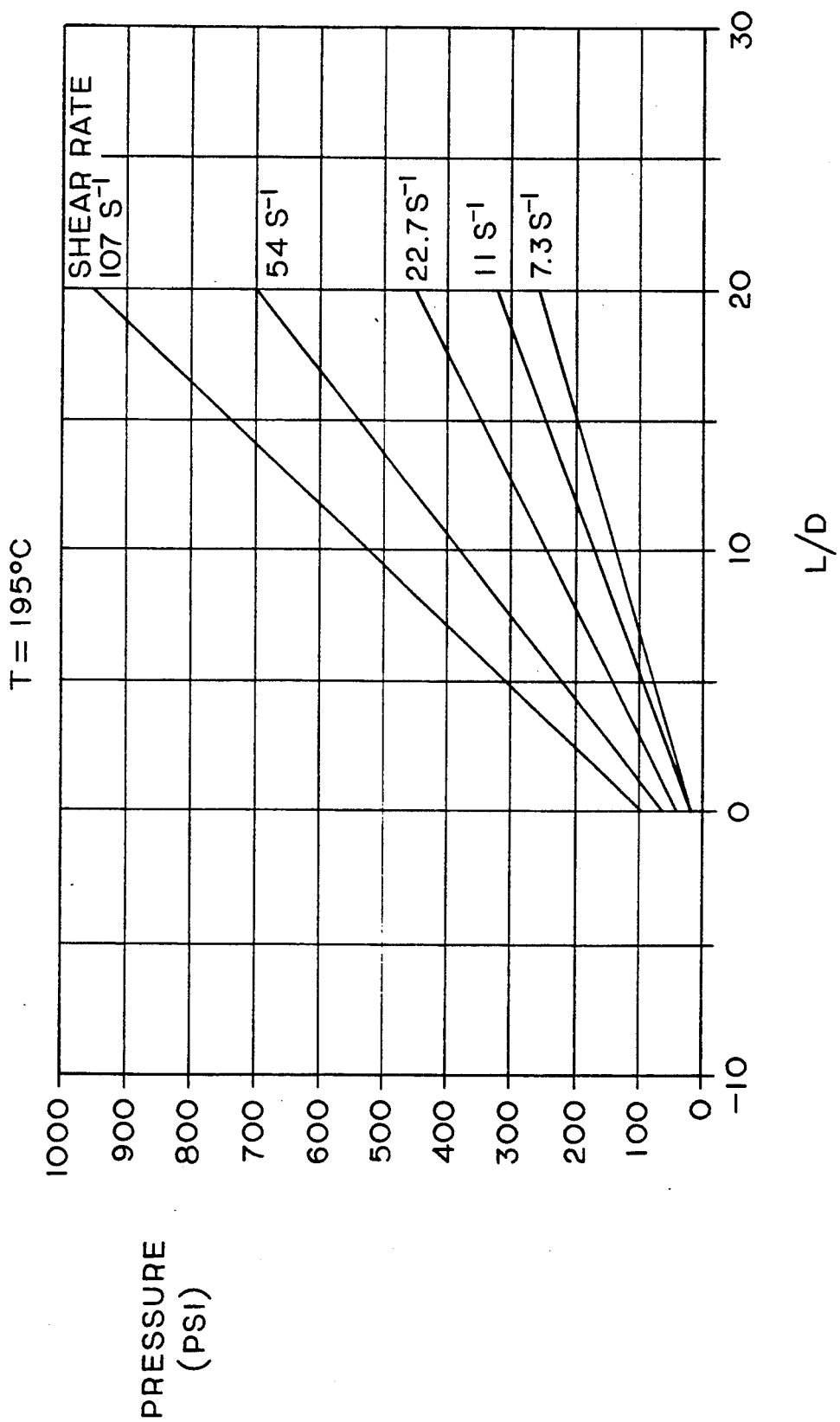
FIG. 4 shows the variation of measured pressure drop with L/D ratio at different shear rates for a low density polyethylene.

To obtain the plot shown in FIG. 1, there may be used a capillary die viscometer which, as indicated above, are commercially available and a zero length die as shown schematically by way of example in FIG. 2, the dies being arranged to receive sample material at controlled rates of flow from an extruder. In the die shown in FIG. 2, a die plate 10 was located at the downstream end of a reservoir 12. The plate 10 had a circular orifice 14 with an entrance angle of 180° and an exit angle of 140°. The orifice diameter was 1 mm and the length as small as practical, in this case 0.3 mm. The plate was of wear-resistant stainless steel. Other suitable wear-resistant materials are, for example, tungsten carbide and diamond. The plot shown in FIG. 1 could in principle be obtained by ensuring that the melt was passed through the two dies at an identical shear rate. In practice, however, it was found more convenient to pass the melt through each die at a range of shear rates, as shown in FIG. 3, to provide plots of pressure drop v. apparent shear rate for dies of different L/D ratios. From these values, there was derived the variation of pressure drop with L/D ratio at different shear rates (FIG. 4), from which the effective shear stress $T_{eff}$ at different shear rates was derived from the equation:

$$T_{eff} = [P_n - P_0]/[4(n-0)] = [P_n - P_0]/4n$$

where $P_n$ is the pressure drop at an L/D ratio of n.

Figure 5:
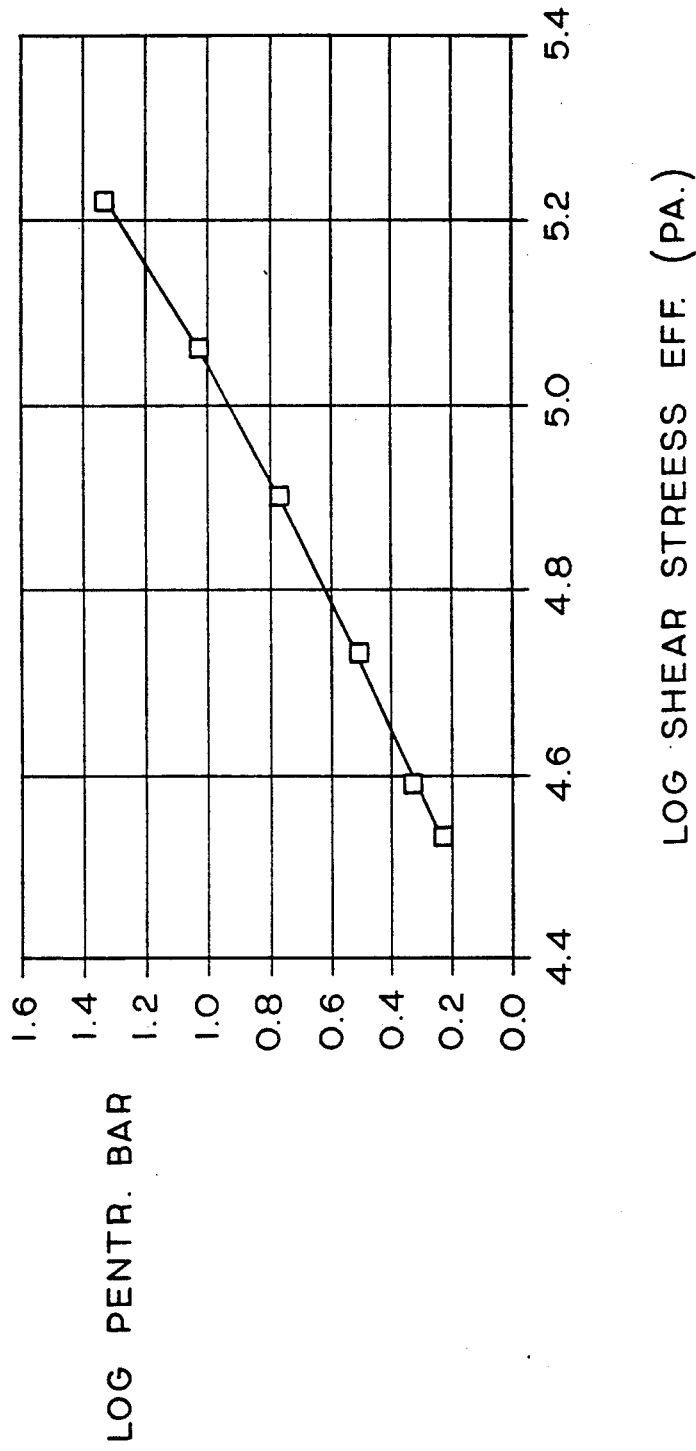
FIG. 5 shows the variation of entrance pressure drop with effective shear stress.

From this there was derived the relationship between $T_{eff}$ and $P_0'$ as shown in FIG. 5.

The measurements discussed above were carried out under operating pressures that give shear stresses similar to those encountered during processing of the polymer. To enable comparisons of the elasticity of different polymers of similar melt index to be made, an arbitrary reference shear stress was chosen and the values of the $P_{ent}$ of the polymers at that shear stress compared. For low density polymers with a melt index from 1 to 25, a shear stress of $10^5$ Pa has provided a convenient reference value.

That the values obtained by the method of the invention are consistent with the results of other measurement methods is shown in the Table below, where various properties of four different samples of low density polyethylene are compared. The four polymers have virtually identical zero-shear viscosities $\eta_0$ and are listed in increasing order of elasticity as measured by accepted tests.

| Polymer | A | B | C | D |
|---|---|---|---|---|
| Melt Index (g/10 min) | 20.6 | 21.8 | 21.6 | 20.6 |
| Density (g/ml) | 0.922 | 0.922 | 0.922 | 0.9145 |
| $\eta_0$ $10^3$ (Pa.s) | 1.90 | 1.89 | 1.95 | 2.04 |
| Recoverable Compliance ($J_e^0 \cdot 10^{-4}$) (Pa$^{-1}$) | 2.01 | 2.49 | 3.33 | 6.18 |
| $C^{13}$ NMR (C$_6$+/1000C) | 3.5 | 3.9 | 4.4 | 5.4 |
| $P_{ent}$ (bar) at $10^5$ Pa shear stress | 4.8 | 4.8 | 6.6 | 8.3 |

As is apparent from the table, steady state recoverable compliance, which is a sensitive measure of polymer melt elasticity, increases through the polymer series A to D, as does the proportion of branch chains of 6 carbon atoms or greater. (The NMR data on long chain branching were confirmed by the results of gel permeation chromatography, the traces of polymers C and D each having a shoulder at short elution times attributable to high molecular weight species, this shoulder being absent from the traces of polymers A and B). The entrance pressure drop of the series follows this order.

Figure 6:
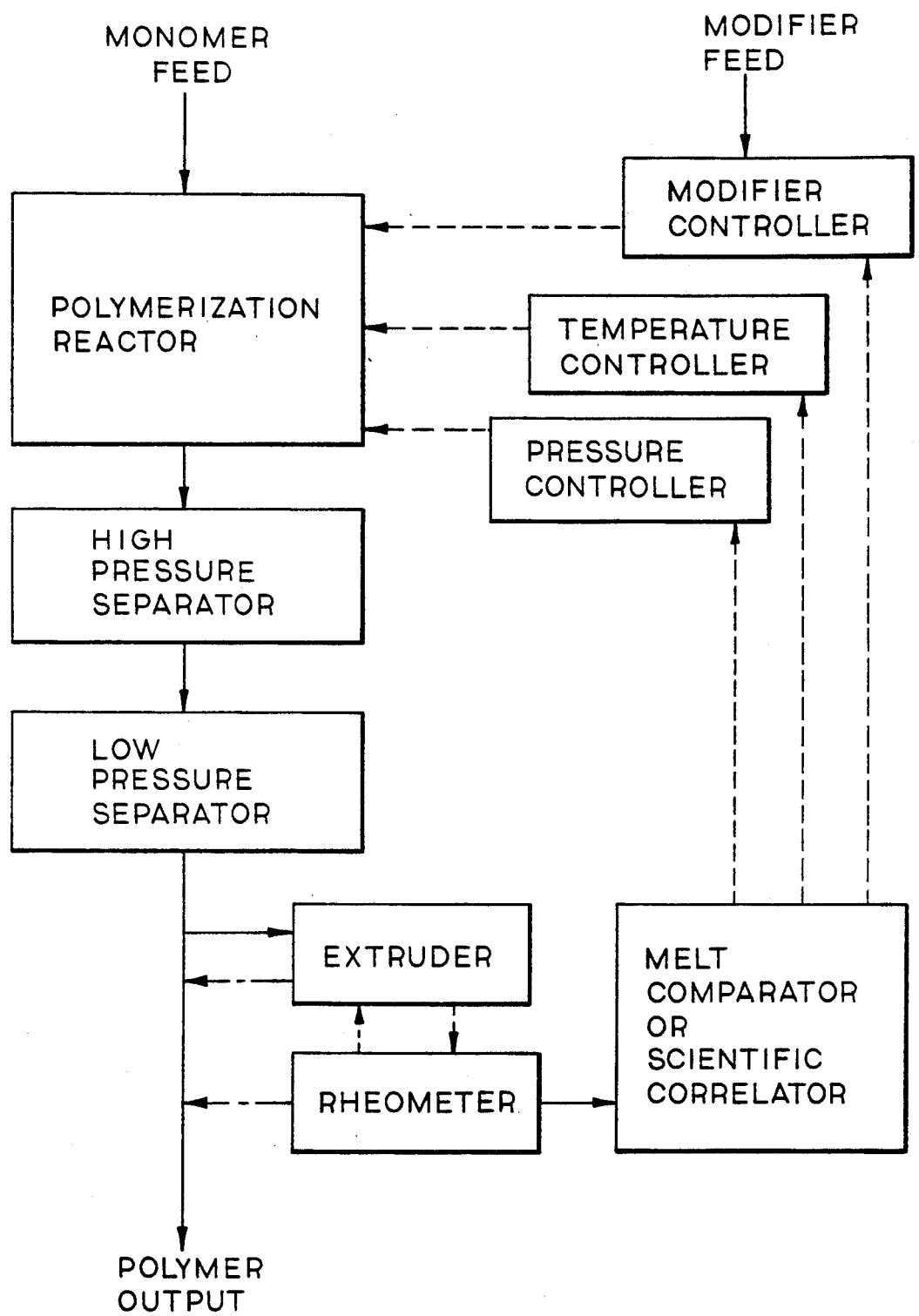
FIG. 6 is a block diagram of a control device according to the invention.

Referring now to FIG. 6, there is shown a block diagram of apparatus constructed in accordance with the invention for the manufacture of a polymer, for example, low density polyethylene or ethylene/propylene copolymer, the polymer structure of which may be controlled by variation in polymerization conditions as known in the art. Examples of such procedures are given in U.S. Pat. Nos. 4,786,697 and 4,874,714, the disclosures of which are incorporated by reference herein. A sample of polymer is fed to an extruder and in turn a sample of material from the extruder barrel is passed to the rheometer and the required properties measured. The polymer output from the extruder may be returned to the polymer product stream, as may rheometer product output, either directly or via the extruder. Information from the rheometer is passed to the comparator which in turn provides information to be used to vary appropriate polymerization conditions, for example comonomer selection and feed rate, catalyst, inhibitor, catalyst reactivator, promoter selection or introduction, pressure, temperature or modifier concentration as required to yield polymer of target properties.

The use of the method of the invention in controlling polymer properties is illustrated by the following.

To adjust drawdown and necking beneficially for extrusion coating using ethylene/acrylic acid copolymers, an integrated polymerization reactor and on-line rheology measuring device according to the invention are employed. Ethylene, acrylic acid, and, optionally, a chain transfer agent are fed to the reactor in varied proportions, and different reactor temperatures are employed to adjust polymer structure, using the measurements of melt elasticity, to yield polymer of optional melt index and desired melt elasticity. By this means, a product of good processability is obtained without the need for prolonged laboratory testing of a range of possibly suitable polymers.

More specifically, three copolymer resins were prepared by high pressure, free-radical copolymerization of ethylene and acrylic acid, each resin having a measured melt index of 1 g/10 min (at 125° C./2.16 kg). Resin 1 was polymerized to contain 7 wt. % acrylic acid and was polymerized at 225° C. under 2100 atm. pressure with transfer agent. Resins 2 and 3 were polymerized to contain 8% acrylic acid at 195° C. and 190° C. respectively. Measurement of the entrance pressure drop was accomplished for each in a rheometer (Rheograph 2002 ®, of Göttfert) fitted with a zero-length capillary die in accordance with the invention. Resin 1 exhibited an entrance pressure drop of 8.3 bars. Resin 2 exhibited one of only 6.3 while resin 3 exhibited one of 6.0 bars. Each resin was then tested for its respective maximum drawdown speed (in meters per minute) in a coextrusion coating line of ER-WE-PA. Normalized results exhibited a value of 1.0 for resin 1, a value of 1.30 for resin 2 and 1.38 for resin 3. Resin 3 thus exhibited a 38% increase in maximum drawdown. These results illustrated that by measuring the entrance pressure drop in accordance with the invention both of comonomer content and polymerization temperature were adjusted to achieve a polymer resin with properties optimized for its processability in the given application.

Various changes and modifications in the products and process of this invention can be made without departing from the spirit and scope thereof. The various embodiments which have been disclosed herein were for the purpose of further illustrating the invention but were not intended to limit it.

I claim:

1. A process for the manufacture of a polymer that is visco-elastic in fluid form, which comprises supplying a feed comprising at least one monomer to a polymerization reactor, polymerizing the feed, recovering the resulting polymer from the reactor, measuring the entrance pressure drop through a narrow die of a sample in fluid form of the polymer recovered from the reactor, computing an elasticity function from the measured entrance pressure drop, comparing said elasticity function of the sample with a target elasticity function or elasticity function range and, if required, adjusting the polymerization process to produce polymer of said target elasticity function or elasticity function range.

2. A process as claimed in claim 1, wherein the elasticity of the sample is monitored by measuring the response of the material to shearing forces, measuring the response of the material to extension forces, and computing a function of the elasticity of the material from the measured responses.

3. A process as claimed in claim 2, wherein the response of the material to shearing forces is obtained by measuring the pressure drop in the material during passage through an elongate die.

4. A process as claimed in claim 2, wherein the response of the material to extension forces is obtained by measuring the pressure drop in the material during passage across a zero length die orifice.

5. A process as claimed in any one of claims 1 to 4, wherein the viscosity is also monitored, and adjustment to reaction conditions is carried out to produce polymer of a target viscosity or viscosity range.

6. A process as claimed in claim 5, wherein the polymer is viscoelastic in the melt, and wherein the elasticity of the polymer melt is monitored.

7. A process as claimed in claim 1, wherein the polymer is polyethylene, an ethylene/propylene copolymer, or an ethylene/acrylic acid copolymer.

* * * * *